United States Patent [19]

Matkovich

[11] Patent Number: 4,952,516

[45] Date of Patent: Aug. 28, 1990

[54] SELF-VENTING DIAGNOSTIC TEST DEVICE

[75] Inventor: Vlado I. Matkovich, Glen Cove, N.Y.

[73] Assignee: Pall Corporation, Glen Cove, N.Y.

[21] Appl. No.: 325,003

[22] Filed: Mar. 17, 1989

Related U.S. Application Data

[63] Continuation of Ser. No. 60,860, Jun. 12, 1987, abandoned.

[51] Int. Cl.$^5$ .............................................. G01N 33/16
[52] U.S. Cl. .................................... 436/170; 422/102; 422/101
[58] Field of Search ..................................... 422/55–61, 422/101, 102, 84–87; 436/169, 170

[56] References Cited

U.S. PATENT DOCUMENTS

| | | | |
|---|---|---|---|
| 3,068,855 | 12/1962 | Furlong | 422/58 |
| 4,195,058 | 3/1980 | Patel | 422/56 |
| 4,201,548 | 5/1980 | Tomaoku et al. | 422/58 |
| 4,223,089 | 9/1980 | Rothe et al. | 422/56 |
| 4,300,910 | 11/1981 | Pannwitz | 422/60 |
| 4,340,565 | 7/1982 | Kitajimi et al. | 422/56 |
| 4,554,133 | 11/1985 | Leichnitz | 422/56 |

FOREIGN PATENT DOCUMENTS

| | | |
|---|---|---|
| 0254794 | 2/1988 | European Pat. Off. |
| 8505451 | 12/1985 | PCT Int'l Appl. |
| 8606004 | 10/1986 | PCT Int'l Appl. |
| 2139519 | 11/1984 | United Kingdom |

Primary Examiner—Christine M. Nucker
Assistant Examiner—T. J. Wallen
Attorney, Agent, or Firm—Leydig, Voit & Mayer

[57] ABSTRACT

A diagnostic test device for detecting the presence of a component in a liquid sample comprises a liquid impervious receptacle vented by a liquophobic element. The receptacle houses an absorbent which contacts and draws liquid through a microporous reaction medium, gas being displaced from the absorbent during the liquid absorption. The liquophobic element vents the displaced gas while ensuring the containment of liquids within the receptacle. The diagnostic test device may also comprise a cover having an aperture communicating with the microporous medium for the application of liquids thereon while providing a liquid impervious seal with a wall of the receptacle. The cover may also force the microporous medium into positive contact with the absorbent to promote absorption.

16 Claims, 3 Drawing Sheets

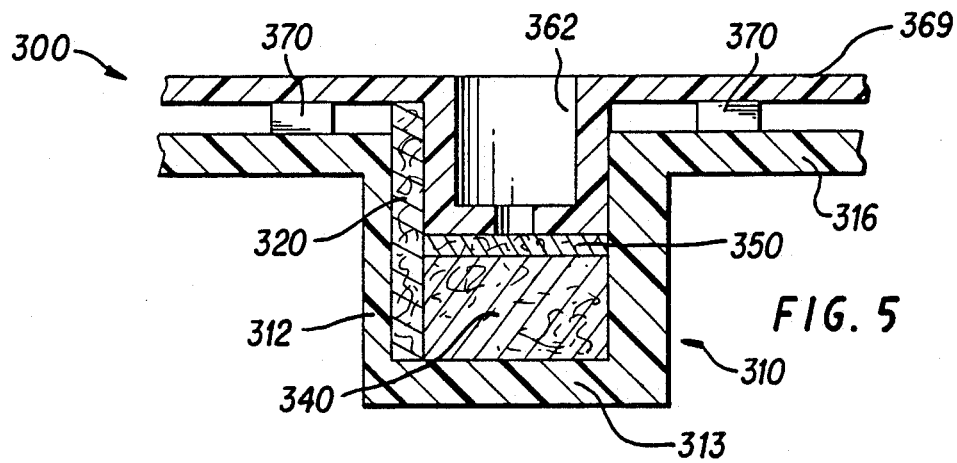
FIG. 5
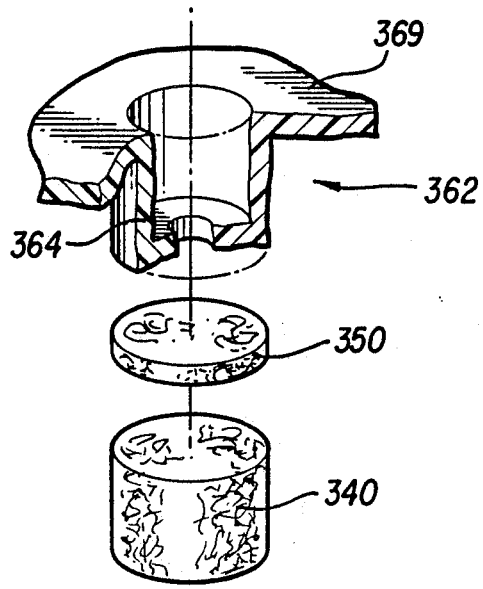
FIG. 6
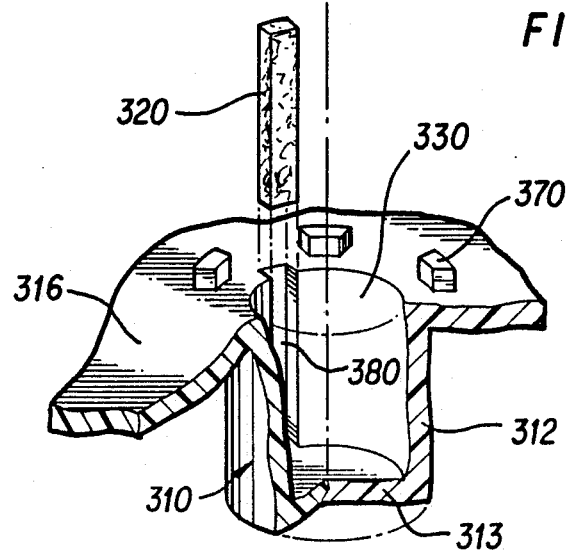

SELF-VENTING DIAGNOSTIC TEST DEVICE

This application is a continuation of application Ser. No. 07/060,860, filed June 12, 1987 abandoned.

FIELD OF THE INVENTION:

The present invention relates to devices for use in the medical field and in particular to diagnostic test devices.

BACKGROUND OF THE INVENTION

In searching a liquid sample for the suspected presence of a specific component, or analyte, it is well known in the art to contact the sample with a liquid containing one or more substances which react with the component, i.e., a biospecific molecule. Detecting a reaction between the component and the biospecific molecule may verify the presence of the suspected component in the sample. It is even possible in some cases to determine the amount of the component present in the sample by measuring the degree of the reaction. The inverse is also true, that is, the absence of a reaction may indicate that the component is not present in the sample.

Diagnostic test devices are routinely used for detecting the presence of a component in a liquid sample. Examples of such tests include immunodiagnostic ELISA assays, RNA and DNA hybridization (gene probe) assays, and microbiological assays. A typical diagnostic test device comprises a receptacle which houses a porous reaction medium, i.e., a medium on or in which a reaction can occur.

In performing an analysis of the liquid sample suspected of containing an analyte, the sample is applied to the reaction medium. In some cases the reaction medium may have been pretreated with the biospecific molecule for that analyte. In other cases it may be added prior to, concurrently, or after application of the sample. To insure complete reaction and enhance the reaction rate, the liquids are drawn through the reaction medium by an absorbent in contact with the reaction medium. The liquids applied to the reaction medium eventually saturate it, come into contact with the surface of the absorbent contacting the medium, and are absorbed into the absorbent.

Conventional diagnostic test devices of the type outlined above have several disadvantages. For example, many conventional diagnostic devices fail to properly vent the receptacle. The materials used as absorbents are porous and initially have air enclosed within the pores. As the liquids are absorbed by the absorbent, air is displaced from the pores. If air is not efficiently vented from the receptacle, the displacement of air from the absorbent will be impaired and the effectiveness of the absorbent will be limited, requiring an unduly large amount of absorbent to absorb the liquids. If the receptacle is completely gas tight, or if during use the receptacle is rendered gas tight, the displacement of air from the absorbent will effectively cease. The absorbent will then fail to absorb the liquids through the reaction medium.

Some conventional devices have provided air venting holes in the receptacle. Unfortunately, these holes not only allow the air to vent but may also allow the liquids to escape from the receptacle. This may be particularly dangerous if the liquid sample or the liquid containing the reactant comprise a contaminated, hazardous, or environmentally harmful substance. Alternatively, some diagnostic test devices have receptacles with air venting holes formed therein which are small enough to allow air to pass without allowing liquids to pass. This design may still fail to vent air because the holes may become blocked by the liquids if the liquids contact the surface in which the holes are formed.

In diagnostic test devices as described above, it is important to provide and maintain good contact between the reaction medium and the absorbent. This insures effective absorption of the liquids through the reaction medium by the absorbent. Good contact also helps in achieving reproducible results by insuring a uniform flow of liquids through the reaction medium.

SUMMARY OF THE INVENTION

The present invention provides an improved diagnostic test device for detecting the presence of a component in a liquid sample. More particularly, the present invention provides a diagnostic test device which safely and effectively vents gas from the receptacle while ensuring containment of liquids inside.

In accordance with the present invention there is provided a diagnostic test device comprising a liquid impervious receptacle housing an absorbent which contacts and draws liquid through a microporous reaction medium, a liquid impervious, liquophobic, gas vent element being cooperatively arranged with the receptacle to vent gas therefrom while retaining liquids. Liquids, such as the sample to be analyzed and reagents used to analyze the sample, are applied to a surface of the microporous medium and wet the same. Thereafter, at least a portion of the liquid contacts and is absorbed into the absorbent abutting the microporous medium. Gas, typically air, is displaced from within the porous absorbent and allowed to vent to the exterior of the receptacle through the liquophobic gas vent while still containing the liquid.

Thus, in accordance with the present invention, a diagnostic test device is provided having a liquid impervious container which reliably contains hazardous or contaminated liquids therein.

Further in accordance with the present invention, a diagnostic test device is provided from which gas, displaced from the absorbent upon the absorption of liquid, is efficiently vented from the receptacle through the liquophobic gas vent thus providing more effective absorption of liquid while using a minimum amount of absorbent.

In another aspect of the invention, a cover is disposed on the microporous medium and has an aperture communicating with the microporous medium.

In accordance with this aspect of the invention, the cover forces the microporous medium into positive contact with the absorbent to promote the absorption of liquid through the medium and into the absorbent while still allowing the application of liquid onto the microporous medium through the aperture.

In yet another aspect of the invention, a diagnostic method is disclosed for detecting the presence of a component in a liquid.

In accordance with the diagnostic method of the present invention, a liquid is applied to a microporous liquophilic medium. An absorbent, disposed in a liquid impervious receptacle and contacting the microporous medium, absorbs the liquid through the microporous medium. Gas is vented from the liquid impervious receptacle through a porous liquophobic element.

BRIEF DESCRIPTION OF THE DRAWINGS

FIG. 5 is a section view of a diagnostic test device according to a third embodiment of the present invention.

FIG. 6 is an exploded view of the diagnostic test device of FIG. 5.

DESCRIPTION OF THE PREFERRED EMBODIMENT

A diagnostic test device according to the present invention generally comprises a liquophobic gas vent element cooperatively arranged with a container to define a liquid impervious interior chamber. For this purpose the liquophobic gas vent may form a portion of the receptacle, for example, a receptacle wall or a portion of a receptacle wall.

Figure 1:
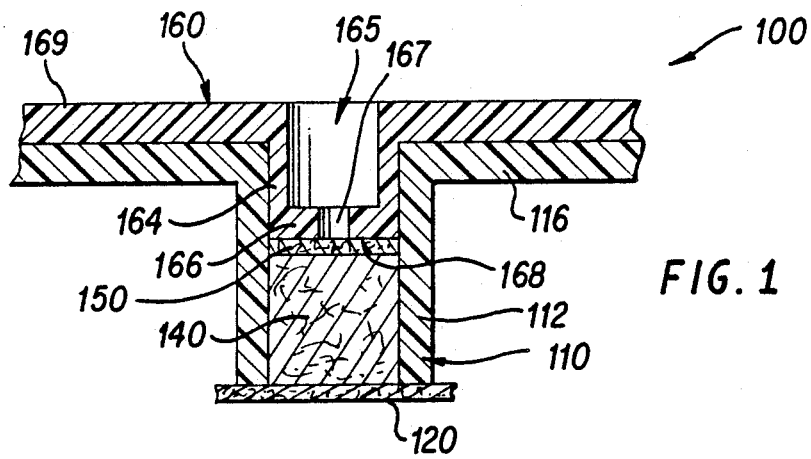
FIG. 1 is a section view of a diagnostic test device according to a first embodiment of the present invention.
Figure 2:
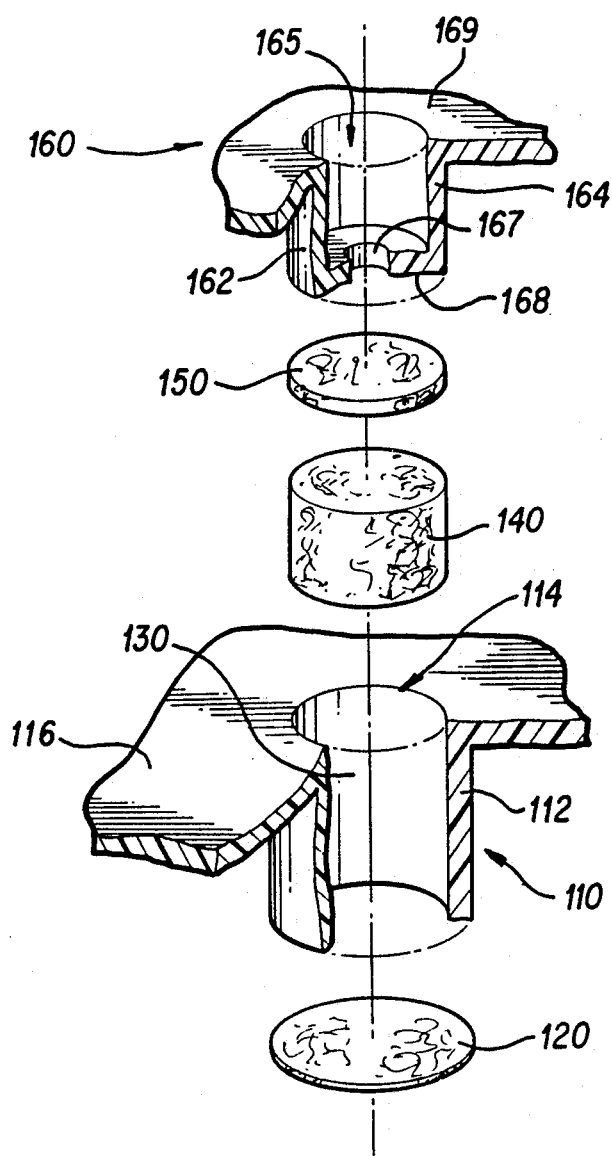
FIG. 2 is an exploded view of the diagnostic test device of FIG. 1.

As shown in FIGS. 1 and 2, in a first exemplary diagnostic test device 100 embodying the present invention the container includes a liquid impervious receptacle 110 and the liquophobic gas vent element forms a liquophobic bottom wall 120 for the receptacle 110. In the illustrated embodiment the receptacle comprises a side wall 112 cooperating with the liquophobic bottom wall 120 to define the interior chamber or bore 130. A porous absorbent 140 is disposed within the bore 130 and a microporous, liquophilic medium 150 abuts the absorbent 120. A liquid sample or a liquid reagent applied to a top surface of the microporous medium 150, after wetting the microporous medium, is drawn through the microporous medium by the absorbent 140 and contained within the bore 130. Air, initially enclosed within the pores of the absorbent 140 and displaced therefrom by the absorption of liquid, is allowed to vent through the liquophobic gas vent 120 without permitting liquid to escape the interior chamber. In accordance with another aspect of the invention, the container may further comprise a cover 160 disposed on the microporous medium 150 forcing the same into positive contact with the absorbent 140.

The receptacle 110, for the purpose of illustration only, takes the form of a well formed by a cylindrical wall 112. However, it is to be understood that any suitably shaped receptacle may be used, for example, the receptacle may be rectangular or oval in cross-section. The well 110 typically may be made of an optically transparent plastic and is liquid impervious. The upper portion of the wall 112 defines a port 114 providing an inlet to the bore 130. The receptacle 110 may further comprise a flange 116 circumscribing the port 114. The flange 116 may be formed integrally with the receptacle wall 112.

The liquophobic gas vent 120 is cooperatively arranged with the receptacle 110 to provide gaseous communication between the exterior of the receptacle, or the environment and the bore 130 for venting gas therefrom. In the preferred embodiment the liquophobic gas vent 120 comprises a porous liquophobic material forming the bottom for the cylindrical well 110. The liquophobic material 120 may be sealed to the well wall 112 by any suitable means to provide a liquid impervious bottom wall for the receptacle.

The absorbent 140 is disposed within the bore 130 and in gaseous communication with the liquophobic gas vent 120. In the embodiment illustrated in FIGS. 1 and 2, the absorbent 140 has upper and lower surfaces, the lower surface of the absorbent 140 contacting the liquophobic bottom 120. Equivalently, because contact between the absorbent and the liquophobic element is not necessary, any arrangement may be used providing gaseous communication between the absorbent and the liquophobic gas vent. That is, the absorbent may be suspended above the liquophobic well bottom by any suitable means such as, for example, supporting the absorbent on a flange extending radially inwardly from the inner wall of the well 110.

The microporous medium 150, comprising a liquophilic material, i.e., a material which is wetted by the applied liquid, abuts the absorbent 140. In the preferred embodiment the microporous medium 150 is disposed within the bore 130 of the receptacle 110. The microporous medium has upper and lower surfaces, the lower surface of the microporous medium 150 contacting the upper surface of the absorbent 140. Liquid contacting the liquophilic microporous medium 150 eventually saturates the same. Thus, the liquid eventually contacts the surface of the absorbent abutting the microporous medium. The microporous medium 150 may be made from a variety of liquophilic materials such as glass fiber, $N_{66}$ polyamide membranes, and varous other high surface area porous membranes. The preparation and use of reaction membranes per se in assays does not in itself constitute a part of the present invention since the preparation and use of such reaction membranes is well known. Rather, the present invention is concerned with the combination of such surfaces, absorbent materials and liquophobic vent membranes. Nevertheless, a brief description of reaction membranes is provided for completeness.

The particular material from which the reaction membrane is formed must not react adversely with substances found in either the samples, reagents, or solvents employed in the analyses. Preferred reaction membranes will be formed from a liquophilic, microporous membrane or other porous material, typically having an absolute pore rating of about 0.001 to about 20 microns, preferably about 0.02 to about 8 microns, and most preferably about 0.2 to about 3 microns. The reaction medium is preferably also skinless. Materials which are suitable for use as the reaction medium typically have voids volumes in the range of from about 60 to about 90%, preferably in the range of from about 75 to about 90%. Preferred materials are hydrophilic in nature and are, therefore, easily water-wettable and tend to freely pass and absorb aqueous solutions. Glass fiber media, such as Pall Corporation's Ultipor GF ® are preferred. Another preferred class of materials are hydrophilic nylon membranes such as those disclosed in U.S. Pat. No. 4,340,479.

The absorbent 140 may comprise porous, absorbent material which does not react adversely as described earlier. It may be formed of hydrophilic fibers, such as cellulose acetate. Other suitable materials include large void-volume microporous membranes, such as $N_{66}$ membranes including Ultipor ® $N_{66}$, BIODYNE ® and LoProdyne$^{TM}$, available from Pall Corporation.

Most preferred are glass fiber media, such as Ultipor GF.

The liquophobic element 120 can be formed from a microporous membrane, which is either treated to render it liquophobic, preferably hydrophobic, or which is inherently liquophobic, preferably hydrophobic. Examples of treated materials are siliconeimpregnated versions of the glass fiber materials mentioned earlier. Preferred are porous, hydrophobic polytetrafluoroethylene membranes, such as Pall Corporation's Emflon ®, with pore sizes in the range of 0.2 to 3 microns.

The cover cooperates with the wall of the interior chamber to provide a liquid impervious seal with the interior chamber wall. The cover can, for example, comprise simply a flat plate arranged in liquid tight contact with the wall 112 defining the interior chamber. In the exemplary embodiment illustrated in FIGS. 1 and 2 however, the cover 160 comprises a cylindrical insert 162 which is intercalated into the bore 130 through the port 114. The cylindrical insert 162 comprises a cylindrical wall 164 having inner and outer surfaces. The outside diameter of the cylindrical insert 162 is chosen such that the outer surface of the cylindrical insert wall 164 is disposed in the bore 130 in liquid tight contact with the inner surface of the side wall 112 of the receptacle 110. Thus, the insert 162 forms a liquid impervious seal with the interior chamber wall, i.e., in the exemplary embodiment, receptacle wall 112. The cover insert 162 further comprises a bottom wall 166 having a lower surface 168 which abuts the upper surface of the microporous medium 150. The inner surface of the cylindrical insert wall 164 and the bottom wall 166 define a recess 165 therein. The bottom wall 166 has an aperture 167 providing fluid communication between the recess 165 and the upper surface of the microporous medium 150. Liquids used in the analysis can be applied to the microporous medium 150 through the aperture 167.

In the preferred embodiment, the cover 160 contacts the upper surface of the microporous medium 150 forcing the same into positive contact with the absorbent 140 to promote absorption of liquid by the absorbent 140. By being disposed on the microporous medium 150, the cover 160 locates the microporous medium in a predetermined position to provide positive contact between the microporous medium 150 and the absorbent 140. The cover includes a flange 169 which, for the purpose of illustration, is shown connected to the upper portion of the cylindrical wall 164 forming the insert 162 and may be formed integrally therewith. The flange 169 cooperates with the well flange 116 to vertically locate the cylindrical insert 162 of the cover 160 in a predetermined position within the bore 130. In the exemplary embodiment in FIGS. 1 and 2, the cover flange 169 has upper and lower surfaces, the lower surface contacting the well flange 116 when the cover 160 is placed on the well 110 and the cylindrical insert 162 is fully inserted in the bore 130.

The well flange 116 and the cover flange 169 may each take any suitable configuration. The shapes of the flanges are not considered to be a limitation of the present invention. Thus, the flanges may be circular or rectangular in plan. Alternatively, when the diagnostic test device of the present invention is used in a multiwell titer plate system, particularly in the context of an automated environment, an insert plate may have an array of multiple projections each forming a cover insert for an individual well. In such a system, the walls and surfaces comprising the insert plate can cooperate with either the walls comprising the multiwell plate or, alternatively, with the upper rims of the cylindrical wells to provide a predetermined vertical position of the cylindrical insert within the respective wells.

In operation of the embodiment shown in FIGS. 1 and 2, liquid, including the sample to be analyzed and/or reagents to be added thereto, may be injected into the recess 165 of the cover 160. The liquid then passes through the communicating aperture 167 in the bottom wall 166 of the recess. Thus, the liquid contacts the upper surface of the microporous medium 150. Because the microporous medium 150 is made of a liquophilic material the microporous medium is wetted by the liquid whereby at least a portion of the liquid then contacts the upper surface of the absorbent 140 which abuts the lower surface of the wetted microporous medium 150. The absorbent 140 then draws the liquid through the microporous medium 150 by absorption. Absorption is enhanced by the cover insert 162 which forces the microporous medium into positive contact with the absorbent. Simultaneously with the absorption of the liquids, air for example, is displaced from the porous absorbent 140 and vented to the exterior of the well 110 through the liquophobic bottom wall 120 The liquophobic bottom allows air to pass through while preventing the passage of liquid. The receptacle 110 and the liquophobic element 120 thus cooperate to both contain liquids within the interior chamber 130 and to vent gases therefrom.

Alternatively, the microporous medium 150 may be coated with at least one of the liquids to be used in the analysis prior to completing the assembly of the device. The other liquids to be used may be added later in the manner described above.

The diagnostic test device of the present invention may also be used with automated test equipment. A multiwell plate may comprise a plurality of wells arranged in a regular pattern or array, the rows and columns of which are individually identified. A given sample can be identified by identifying the row and column of the well in which it is analyzed. The automated machinery can be programmed to perform the steps comprising the test procedure For example, a liquid may be simultaneously added to several or all of the wells comprising a multiwell plate. Also, several biochemical liquids or reagents may be sequentially added to select wells at predetermined intervals, i.e., the automated machinery may pause between the addition of liquids to allow reaction or absorption time.

In the event that a chemical or biochemical reaction takes place, for example, a color change, indicative of the presence of a suspected component in the sample, quantification of the component may be carried out by known methods. For example, if the wells of the multiwell plate are made of an optically transparent plastic, a spectral analysis of the reaction may provide the quantification desired. The plate is moved to a station in the automated machinery where a given well is exposed to a light of a specific wavelength. A photodetector coaxial with the well and light source reads the intensity of the transmitted light reflected through the well. The intensity can be correlated with a quantity of the component present in the sample.

Figure 3:
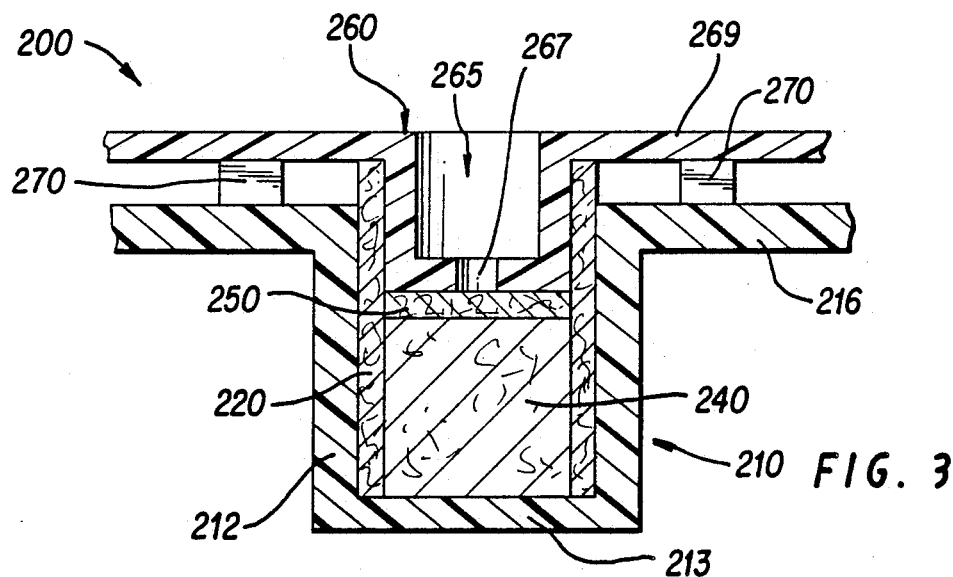
FIG. 3 is a section view of a diagnostic test device according to a second embodiment of the present invention.
Figure 4:
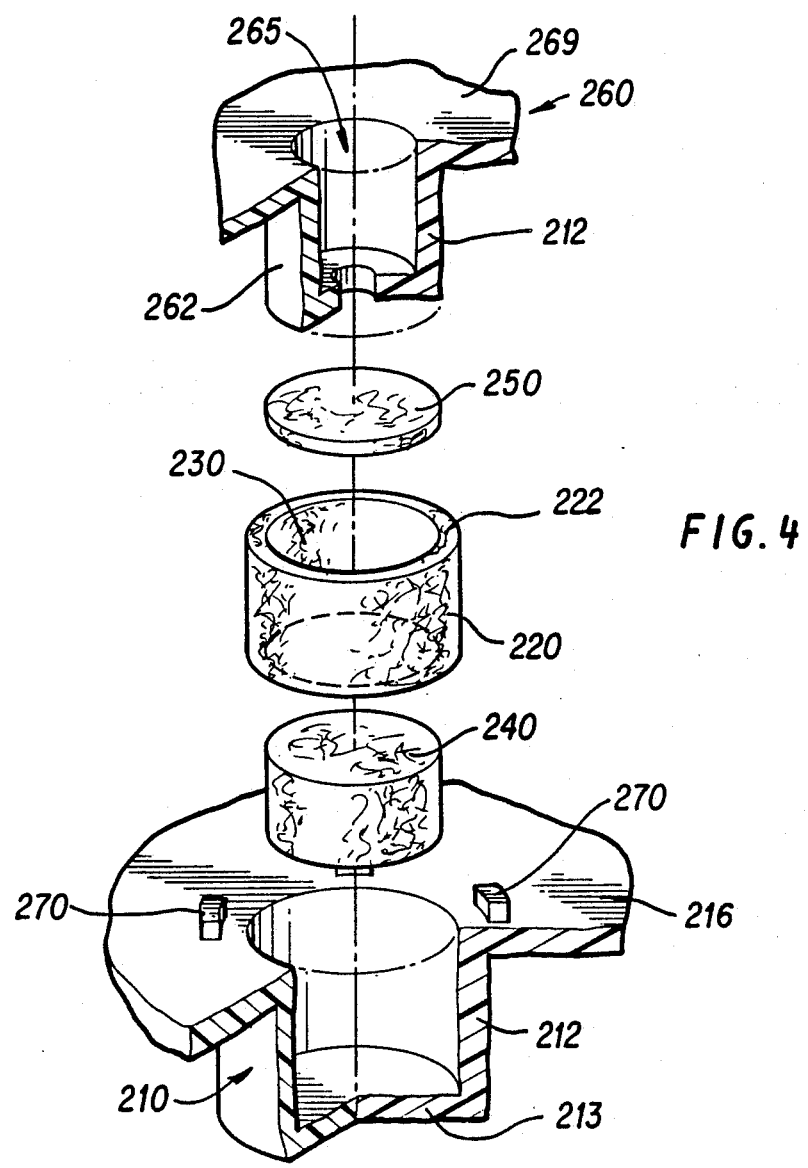
FIG. 4 is an exploded view of the diagnostic test device of FIG. 3.

In a second exemplary diagnostic test device 200 as shown in FIGS. 3 and 4, only those components which are new or modified are discussed in detail here. Those elements which are omitted in this discussion are understood, for the purpose of illustration, to be substantially the same as in the first exemplary embodiment.

In the second embodiment, the receptacle comprises a cylindrical well 210 having a liquid impervious bottom wall 213. The bottom 213 of the well may be made integrally with, and of the same material as the cylindrical wall 212 of the well, i.e., the well may be made of an optically transparent plastic or any other suitable liquid impervious material. In the embodiment of FIGS. 3 and 4, the liquophobic gas vent comprises an element, at least a portion of which is disposed within the receptacle and provides gaseous communication between the interior chamber and the environment. For this purpose, the liquophobic element comprises a liquophobic sleeve 220 which is inserted within the cylindrical well 210. The liquophobic sleeve 220 may take the same shape as the well 210 and thus, in the embodiment illustrated in FIGS. 3 and 4, it is cylindrical. In the exemplary embodiment shown, the liquophobic sleeve 220 lines and intimately contacts the inner surface of the cylindrical wall 212. Thus a bore 230, defining the interior chamber and analogous to the bore 130 in the first embodiment, is defined by the inner surface of the cylindrical liquophobic sleeve 220 and the end wall 213 of the receptacle 210. Alternatively, the liquophobic sleeve 220 may have an end wall itself thus defining the interior chamber therein.

An absorbent 240, a microporous medium 250, and a cylindrical cover insert 262, all substantially the same as that described in the first exemplary embodiment, are stacked within the bore 230 of the liquophobic sleeve 220 and abut each other as described in the first embodiment That is, the absorbent 240 rests on the bottom 213 of the cylindrical well 210. The microporous medium 250 is disposed on the upper surface of the absorbent. The cylindrical insert 262 of the cover contacts the upper surface of the microporous medium 250 and vertically locates the same in a predetermined position to provide positive contact between the microporous medium and the absorbent 240. In the embodiment illustrated in FIGS. 3 and 4, the absorbent 240 is in contact with the liquophobic element 220. However, it is understood that the absorbent 240 and the liquophobic element 220 may be spaced from each other and need only have gaseous communication established therebetween.

In the embodiment of FIGS. 3 and 4, the cover again cooperates with the interior chamber wall to provide a liquid impervious seal. That is, the cover insert 262 is disposed within the liquophobic sleeve 220 in liquid tight contact with the inner chamber wall, i.e., with the inner surface of the liquophobic sleeve 220.

The cover 260 of the second embodiment differs from that of the first embodiment in the manner in which it is disposed on the well. Spacer elements 270 are disposed between the well flange 216 and the cover flange 269. The spacer elements 270 may be formed integrally as part of either flange or, alternatively, may be separate elements. In the embodiment illustrated in FIGS. 3 and 4, the spacer elements 270 comprise knobs formed integrally with the well flange 216 on the upper surface thereof. The spacer elements 270 are radially disposed in an intermittent manner about the well port and separate the flanges to allow air passage between adjacent spacers and between the flanges Thus, air, venting through the liquophobic sleeve 220, may escape. Alternatively, the liquophobic sleeve 220 may project vertically beyond the well flange as shown in FIG. 3. The cover flange 269 may rest on an upper rim 222 of the liquophobic sleeve thus leaving a space between the cover flange 269 and the well flange 216 defining an air passage therebetween.

In operation of the diagnostic test device according to this embodiment, as in the first embodiment, liquids are injected into the recess 265 of the cover insert 262 and contact the upper surface of the microporous medium 250 by passing through the communicating aperture 267. The liquids are then drawn through the microporous medium and into the absorbent 240. As liquid is absorbed by absorbent, air is displaced therefrom and vented through the surrounding liquophobic sleeve 220 which acts as a gas vent. As mentioned above, air escapes from the receptacle through the air passage provided between the well flange 216 and the cover flange 269. Although air is allowed to escape from the receptacle, liquids are still securely contained therein. To provide greater assurance of liquid containment, both the well and the liquophobic sleeve 220 may be relatively tall as compared with the level of liquid introduced therein In FIGS. 5 and 6 there is shown a third exemplary diagnostic test device 300 embodying the present invention. Again, only modified or new elements are discussed in detail According to this embodiment, the receptacle comprises a liquid impervious cylindrical well 310 comprising a cylindrical side wall 312 and a bottom wall 313, both walls having inner surfaces Again, the liquophobic gas vent comprises an element, at least a portion of which is disposed within the receptacle and provides gaseous communication between the interior chamber and the environment. For this purpose, a groove or keyway 380 is formed in the inner surface of the cylindrical wall 312. The keyway may take any suitable configuration. For the purpose of illustration only, the keyway 380 has a rectangular cross section. The liquophobic vent in this embodiment takes the form of a rectangular column of liquophobic material 320 having a cross section substantially the same as that of the keyway 380. The liquophobic column 320 is inserted in the keyway 380 and thus forms a portion of the inner surface of the cylindrical wall 312.

In this embodiment, the interior chamber comprises a bore 330 defined by the inner surfaces of the side and bottom walls of the receptacle, 312 and 313, respectively, and by the liquophobic column 320.

Again, for the purpose of illustration, the cover insert 362, the microporous medium 350, and the absorbent 340 are disposed within the bore 330 in a stacked relationship as described above. In the exemplary embodiment, the absorbent has a surface contacting the liquophobic column 320. When liquids are absorbed into the absorbent, air is displaced into the liquophobic column 320 without allowing liquids to escape from the receptacle 310. Again, spacer elements may be provided between the well flange 316 and the cover flange 369 to create an air escape passage Also, the cover cooperates with the interior chamber wall to provide a liquid impervious seal, i.e., the cover insert is disposed within the bore 330 in liquid tight contact with both the receptacle wall and the liquophobic column.

In an alternative construction the keyway 380 can be formed in the outer surface of the cover insert wall 364. In this case the column 320 is disposed in this keyway and still provides gaseous communication between the interior chamber or bore 330 and the environment.

As will be evident to those skilled in the art, various modifications on this invention can be made without departing from the spirit or scope thereof; and therefore, it is not intended to be limited except as indicated in the following claims.

I claim:

1. A diagnostic test device comprising:
    a liquid impervious receptacle having an aperture;
    a gas permeable hydrophobic element forming at least part of one wall of said receptacle and adapted for venting gas therefrom while resisting passage of liquids;
    an absorbent disposed within the receptacle;
    a hydrophilic microporous reaction medium for a diagnostic test reagent disposed over the aperture in the receptacle, said reaction medium having an absolute pore size of from 0.002 to 20 microns and having first and second surfaces, the first surface contacting the absorbent; and
    a cover disposed on the second surface of the microporous reaction medium, the cover having an aperture communicating with the second surface of the microporous reaction medium.—.

2. A diagnostic test device according to claim 1 wherein the absorbent contacts the hydrophobic element.

3. A diagnostic test device according to claim 1 wherein the cover comprises an insert defining a recess and wherein the aperture provides fluid communication between the recess and the second surface of the microporous medium.

4. A diagnostic test device according to claim 1 wherein the hydrophobic element forms at least a portion of the receptacle.

5. A diagnostic test device according to claim 4 wherein the cover comprises an insert disposed in the receptacle in liquid tight contact with the receptacle wall.

6. A diagnostic test device according to claim 4 wherein the hydrophobic element provides a liquid impervious bottom wall for the receptacle.

7. A diagnostic test device according to claim 1 wherein the receptacle has an exterior and at least a portion of the hydrophobic element is disposed within the receptacle in gaseous communication with the exterior of the receptacle.—.

8. A diagnostic test device according to claim 7 wherein the receptacle and the hydrophobic element define an interior chamber and wherein the cover is in liquid tight contact with the interior chamber wall .—;

9. A diagnostic test device according to claim 8 wherein the cover comprises an insert disposed within the interior chamber in liquid tight contact with the interior chamber wall.

10. A diagnostic test device according to claim 7 wherein the receptacle comprises a wall defining a groove therein and wherein the hydrophobic element comprises a column disposed within the groove.

11. A diagnostic test device according to claim 10 wherein the receptacle and the hydrophobic column define a wall forming an interior chamber and wherein the cover comprises an insert disposed within the interior chamber in liquid tight contact with the interior chamber wall.

12. A diagnostic test device comprising:
    a liquid impervious receptacle having an aperture;
    a gas permeable hydrophobic element forming at least part of one wall or said receptacle and adapted for venting gas therefrom while resisting passage of liquids wherein the hydrophobic element comprises a hydrophobic sleeve disposed at least partially within the receptacle in gaseous communication with the exterior of the receptacle;
    an absorbent disposed within the receptacle;
    a hydrophilic microporous reaction medium for a diagnostic test reagent disposed over the aperture in the receptacle, said reaction medium having an absolute pore size of from 0.002 to 20 microns and having first and second surfaces, the first surface contacting the absorbent; and
    a cover disposed ion the second surface of the microporous reaction medium, the cover having an aperture communicating with the second surface of the microporous reaction medium.—;

13. A diagnostic test device according to claim 12 wherein the cover comprises an insert disposed within the hydrophobic sleeve in liquid tight contact with the sleeve.

14. A diagnostic test device according to claim 12 wherein the absorbent is disposed within the hydrophobic sleeve and contacts the hydrophobic sleeve.

15. A diagnostic method for detecting a component in a liquid, comprising:
    applying the liquid to a first surface of a microporous hydrophilic reaction medium having a second surface in contact with an absorbent disposed within a liquid impervious receptacle, said reaction medium bearing a diagnostic reagent and having an absolute pore size of from 0.002 to 20 microns;
    absorbing at least a portion of the liquid through the microporous hydrophilic medium into the absorbent; and
    venting gas displaced from within the receptacle by the liquid through a gas permeable but hydrophobic element forming at least a part of one wall of said receptacle.—.

16. The diagnostic method of claim 15 wherein, when liquid is absorbed into the absorbent, gas is displaced from the absorbent and wherein the displaced gas is vented from the receptacle through the hydrophobic element.

* * * * *